(12) United States Patent
McDougall

(10) Patent No.: US 6,421,866 B1
(45) Date of Patent: Jul. 23, 2002

(54) ELECTRIC TOOTHBRUSH

(76) Inventor: Gregory John McDougall, 10-A Taichi Court, 132 Austin Road, Tsim Sha Tsui, Kowloon (HK)

( * ) Notice: Subject to any disclaimer, the term of this patent is extended or adjusted under 35 U.S.C. 154(b) by 29 days.

(21) Appl. No.: 09/740,433

(22) Filed: Dec. 19, 2000

(51) Int. Cl.⁷ .............................................. A46B 13/02
(52) U.S. Cl. ........................................ 15/22.1; 15/21.1
(58) Field of Search ................................ 15/21.1, 22.1, 15/22.2, 28, 29

(56) References Cited

U.S. PATENT DOCUMENTS 5,165,131 A * 11/1992 Staar
5,189,751 A * 3/1993 Guiliani et al.
5,247,716 A * 9/1993 Bock
5,511,270 A * 4/1996 Eliachar et al.
5,911,256 A * 6/1999 Tsai
5,974,613 A * 11/1999 Herzog
5,974,615 A * 11/1999 Schwarzt-Hartmann et al.
5,987,681 A * 11/1999 Hahn et al.
6,092,252 A * 7/2000 Fischer et al.
6,322,583 B1 * 11/2001 Tu et al.
6,347,425 B1 * 2/2002 Fattori et al.

* cited by examiner

Primary Examiner—Terrence R. Till
(74) Attorney, Agent, or Firm—Jackson Walker L.L.P.

(57) ABSTRACT

An electric toothbrush has a balanced mass provided on a shaft extension that rotates freely about a longitudinal axis, inside a cavity in a brush head The shaft extension and the brush head are flexibly coupled to a drive shaft and to a remote end of a shank respectively. When the shaft is rotated by an electric motor in a handle, of the toothbrush, an off-set stub axle, effectively at a remote end of the shaft extension and fitted to a bearing in the brush head, causes the brush head to vibrate. The shank is not caused to vibrate to any extent.

7 Claims, 1 Drawing Sheet

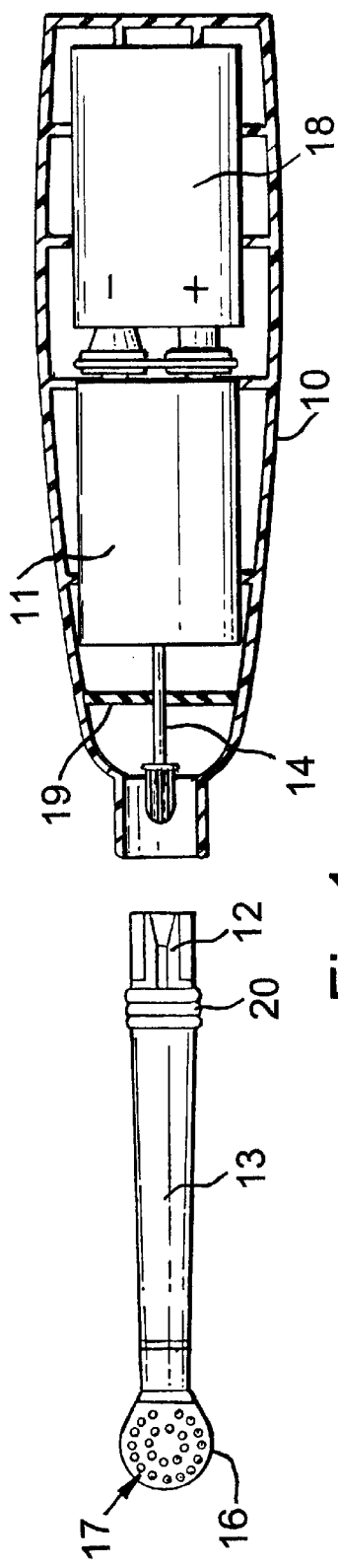
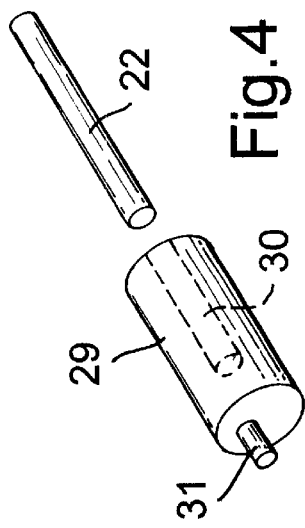
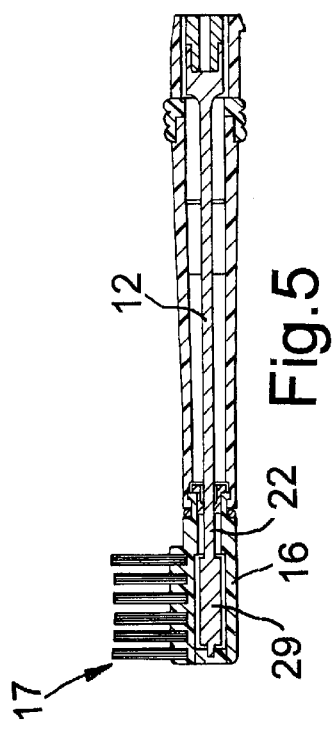
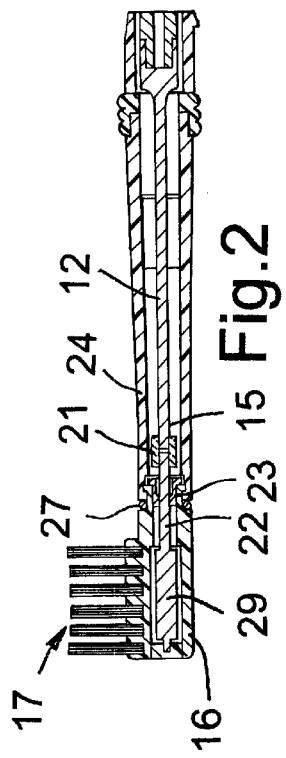
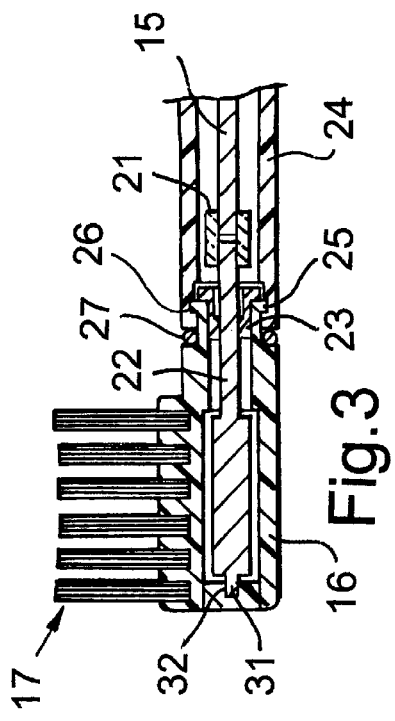

ELECTRIC TOOTHBRUSH

BACKGROUND OF THE INVENTION

1. Field of the Invention

The invention relates to electric toothbrushes.

2. Description of Prior Art

Many toothbrushes are known and widely used having a set of bristles mounted to a brush head that is driven by an electric motor inside a toothbrush handle. The motor may be powered by a battery, also inside the handle, or from a power supply socket adjacent a point-of-use. As such, the brush head can be rotated and/or vibrated by the motor to enhance the operation of the toothbrush for cleaning teeth. For vibrating the brush head, it is already known to provide an eccentrically mounted weight inside the handle directly coupled to the motor. As a result the handle is vibrated and this vibration is transmitted to the brush head in use via a shank of the toothbrush. This means that the user's hand is vibrated. Inherently the vibrations are dampened by the user's grip. When using the toothbrush, the handle vibrations are not comfortable for the user and waste, in effect, considerable mechanical energy that must be supplied by the motor.

It is also known in U.S. Pat. No. 5,987,681 to mount an unbalanced mass on the drive shaft near a brush head but movement of a shank of the toothbrush also uses up, or wastes, energy that must be provided by the motor.

SUMMARY OF THE INVENTION

It is an object of the invention to overcome or to at least reduce these problems.

According to the invention there is provided an electric toothbrush having an elongate handle, an electric motor inside the handle, a drive shaft rotatable about a longitudinal axis of the toothbrush inside an elongate shank a brush head mounted at a remote end of the shank carrying bristles extending general transversely to the longitudinal axis from the brush head, a drive shaft extension formed with a balanced mass freely rotatable within a cavity in the brush head about said longitudinal axis, and an axle having an axis is off-set from the longitudinal axis which mechanically couples the brush head to a remote end of the drive shaft extension, in which the brush head is flexibly coupled to the remote end of the shank, such that when the drive shaft is rotated the brush head is caused to vibrate relative to the shank.

The drive shaft may be supported by a bearing, on the longitudinal axis, that is mounted adjacent the remote end of the shank.

The shaft extension may comprise a shaft rotatable about the longitudinal axis and a uniform sleeve that fits over the shaft to form the balanced mass.

The sleeve is preferably made of metal.

The brush head and the remote end of the shank may be flexibly coupled together by a coupling formed by integrally formed resilient engaging formations on mating surfaces of the brush head and the remote end of the shank, and a resilient O-ring separating the mating surfaces.

A resilient tube may be provided that drivingly connects the shaft extension to the drive shaft.

The drive shaft and the drive shaft extension may be integrally formed.

BRIEF DESCRIPTION OF THE DRAWINGS

An electric toothbrush according the invention will now be described with reference to the accompanying drawings in which:

FIG. 1 is an exploded part-sectioned plan view of the toothbrush;

FIG. 2 is a sectioned side view of part of the toothbrush; and

FIG. 3 shows view an enlarged sectioned side view of part of FIG. 2;

FIG. 4 shows an isometric view of a drive shaft extension for the toothbrush; and FIG. 5 is a sectioned side view of an alternative arrangement of FIG. 2.

DESCRIPTION OF THE PREFERRED EMBODIMENT

Referring to the drawings, in FIG. 1 the toothbrush has an elongate handle 10 and a motor 11 mounted inside the handle. A drive shaft 12, that is rotatable about a longitudinal axis of the toothbrush inside a shank 13, is releasably coupled in use at one end to a rotor 14 of the motor. A remote end 15 of the drive shaft is connected, as described below, to a brush head, 16 that has a set of bristles 17 extending from the brush head in a direction generally transverse to the said longitudinal axis. A battery pack 18 inside the handle provides power for the motor 11. One rubber seal 19 is mounted inside the handle and another rubber seal 20 is provided to seal and connect the shank 13 to the handle 10.

In FIG. 2, the remote end 15 of the drive shaft 12 is rotationally gripped by a resilient tube 21 that fits to a drive shaft extension 22. The shaft extension is rotatably supported by a bearing 23 provided in the brush head 16 adjacent a remote end 24 of the shank 13. The brush head 16 is flexibly connected to the remote end 24 by a flexible coupling.

The flexible coupling, as better seen in FIG. 3 and provided by resilient formations comprises an integrally molded circular flexible clip 25 formed adjacent a mating surface of the brush head 16 that spring-fits into a groove 26 integrally formed adjacent a mating surf ace at the remote end 24 of the shank. The two mating surfaces are separated by a rubber O-ring 27.

The drive shaft extension 22 is formed of two components (see FIG. 4), that comprise the drive shaft 22 and a closed metal sleeve 29 that has an central channel 30 in which the shaft 22 fits and is fixed. The sleeve has a stub axle 31, that is off-set with respect to the said longitudinal axis about which the drive shaft extension rotates in use. The stub axle 31 mechanically connects the sleeve, and hence a remote end of the shaft extension 22, to an axle bearing aperture 32 inside the brush head 16. As a result, when the drive shaft 12 rotates the brush head 16 is caused to vibrate relative to the shank 13.

Importantly, these vibrations are not transferred, i.e. reflected, to any major extent along the shank to the handle 10 so that the toothbrush is comfortable to use. In fact, the shank 13 vibrates very little, if at all. Also, the effective energy required to generate the vibrations is significantly less than in prior art arrangements, especially where vibrations are generated inside the handle and transferred by the shank to the brush head. As explained earlier, a major energy disadvantage in that prior art is that the user inherently dampens the vibrations by gripping the handle quite tightly and so a lot of energy is wasted. Also, in embodiments of this invention the shank does not or has little tendency to flex when the brush head is vibrated. In fact the main purpose of the balanced mass (the sleeve 29) is to resist any reflected vibrations that may occur in the drive shaft 12. The balanced mass provides significant dynamic inertia to retain the drive shaft extension 22 to rotate about the said longitudinal axis.

The stub axle 30 is preferably off-set from the longitudinal axes by about 0.5 mm. It is generally preferable for creating suitable vibrations in the described embodiment to run the drive shaft 12 at between 10000 and 12000 revolutions per minute. However much lower speeds may provide efficient and effect teeth cleaning because the vibrations caused by the off-set stub axle are quite complex. The vibrations caused in the brush head have a circular component that is believed to enhance the brushing effect because the bristles are moved not only up and down but also, to some extent, side to side.

It will be appreciated that the toothbrush may have a single tuft of bristles so that the toothbrush may form and be used as a 'tooth pick'.

The effective amount of brush head vibration can be changed to alter the characteristics of the vibrations. In general, the more off-set the stub axle 31 is from the longitudinal axis, or the heavier the mass 29, the 'harder' the tooth brushing effect will be. Thus, it is a quite simple matter to arrange for so-called hard, medium, and soft vibration/brushing effects, by using different amounts of stub axle off-sets, different masses and/or driving the shaft 12 at different speeds, to suit different user requirements.

In FIG. 5, the arrangement is the same as shown in FIG. 2 except that the drive shaft 12 is integrally formed with the drive shaft extension 22. The balanced mass 29 may also be integrally formed with the shaft 22 or, for example, provided a mold insert when the shaft is formed. The stub axle 31, see FIG. 4, may also be integrally formed with the shaft 22 and/or mass 29.

In the embodiments, the flexible coupling is provided by interlocking formations and an O-ring. It will be appreciated that many other forms of flexible coupling may be used.

I claim:

1. An electric toothbrush having an elongate handle, an electric motor inside the handle, a drive shaft rotatable about a longitudinal axis of the toothbrush inside an elongate shank, a brush head mounted at a remote end of the shank carrying bristles extending general transversely to the longitudinal axis from the brush head, a drive shaft extension formed with a balanced mass freely rotatable within a cavity in the brush head about said longitudinal axis, and an axle having an axis that is off-set from the longitudinal axis which mechanically couples the brush head to a remote end of the drive shaft extension, in which the brush head is flexibly coupled to the remote end of the shank, such that when the drive shaft is rotated the brush head is caused to vibrate relative to the shank.

2. An electric toothbrush according to claim 1, in which the drive shaft is supported by a bearing, on the longitudinal axis, that is mounted adjacent the remote end of the shank.

3. An electric toothbrush according to claim 1, in which the shaft extension comprises a shaft rotatable about the longitudinal axis and a uniform sleeve that fits over the shaft to form the balanced mass.

4. An electric toothbrush according to claim 3, in which the sleeve is made of metal.

5. An electric toothbrush according to claim 1, in which the brush head and the remote end of the shank are flexibly coupled together by a coupling formed by integrally formed resilient engaging formations on mating surfaces of the brush head and the remote end of the shank, and a resilient O-ring separating the mating surfaces.

6. An electric toothbrush according to claim 1, including a resilient tube that drivingly connects the shaft extension to the drive shaft.

7. An electric toothbrush according to claim 1 in which the drive shaft and the drive shaft extension are integrally formed.

* * * * *